US008164976B2

(12) United States Patent
Moore et al.

(10) Patent No.: US 8,164,976 B2
(45) Date of Patent: Apr. 24, 2012

(54) ACOUSTIC SYSTEM QUALITY ASSURANCE AND TESTING

(75) Inventors: G. Wayne Moore, Lyons, CO (US); James M. Gessert, Colorado Springs, CO (US); John G. Timms, Longmont, CO (US); Matthew Fitzgibbons, Colorado Springs, CO (US)

(73) Assignee: Unisyn Medical Technologies, Inc., Golden, CO (US)

( * ) Notice: Subject to any disclaimer, the term of this patent is extended or adjusted under 35 U.S.C. 154(b) by 386 days.

(21) Appl. No.: 12/536,744

(22) Filed: Aug. 6, 2009

(65) Prior Publication Data
US 2011/0030448 A1 Feb. 10, 2011

(51) Int. Cl.
*G01N 29/00* (2006.01)
*G01S 15/00* (2006.01)

(52) U.S. Cl. .......................................... 367/13; 73/1.82

(58) Field of Classification Search .................. 367/13; 73/1.82
See application file for complete search history.

(56) References Cited

U.S. PATENT DOCUMENTS

| | | | |
|---|---|---|---|
| 3,863,198 A | 1/1975 | Lerner | |
| 4,073,608 A | 2/1978 | Christy | |
| 4,241,713 A | 12/1980 | Crutchfield | |
| 4,313,216 A | 1/1982 | Jaeger et al. | |
| 4,830,593 A | 5/1989 | Byram et al. | |
| 4,998,867 A | 3/1991 | Sakamaki et al. | |
| 5,427,068 A | 6/1995 | Palmer | |
| 5,489,199 A | 2/1996 | Palmer | |
| 5,522,356 A | 6/1996 | Palmer | |
| 6,526,937 B1 | 3/2003 | Bolonkin | |
| 6,659,066 B1 | 12/2003 | Lee | |

(Continued)

FOREIGN PATENT DOCUMENTS
CA 2612386 A1 12/2006

OTHER PUBLICATIONS

Notification of Transmittal of the International Search Report and the Written Opinion of the International Searching Authority, or the Declaration. Applicant: Unisyn Medical Technologies. International Application No. PCT/US 10/44763. International Filing Date: Aug. 6, 2010. Mailing Date: Dec. 17, 2010.

*Primary Examiner* — Daniel Pihulic
(74) *Attorney, Agent, or Firm* — Marsh Fischmann & Breyfogle LLP

(57) ABSTRACT

Embodiments of the invention provide for testing acoustic systems. According to one embodiment, testing an acoustic system can comprise receiving a signal from the acoustic system at a testing device via one of a plurality of channels between the acoustic system and the testing device. At least one pulse from a pattern pulses of the signal can be detected with the testing device by matching the pattern of pulses to an expected pulse pattern for the acoustic system. For example, matching the pattern of pulses to an expected pulse pattern can comprise determining whether the pulse pattern includes a first pulse type. If the pulse pattern includes the first pulse type, a determination can be made whether the pulse pattern further includes a second pulse type. If the pulse pattern further includes the second pulse type, a subsequent pulse of the second pulse type can be identified and detected.

21 Claims, 9 Drawing Sheets

U.S. PATENT DOCUMENTS

| | | | |
|---|---|---|---|
| 7,028,529 B2 | 4/2006 | Gessert et al. | |
| 7,155,957 B2 | 1/2007 | Gessert et al. | |
| 7,278,289 B2 | 10/2007 | Gessert et al. | |
| 7,487,131 B2 | 2/2009 | Harris et al. | |
| 2011/0030448 A1* | 2/2011 | Moore et al. | 73/1.82 |
| 2011/0032793 A1* | 2/2011 | Moore et al. | 367/13 |
| 2011/0032799 A1* | 2/2011 | Moore et al. | 367/95 |

* cited by examiner

ACOUSTIC SYSTEM QUALITY ASSURANCE AND TESTING

CROSS-REFERENCES TO RELATED APPLICATIONS

This application is related to the following concurrently filed, commonly assigned U.S. patent applications, the entire disclosure of each of which is incorporated herein by reference in its entirety for all purposes: U.S. patent application Ser. No. 12/536734 by G. Wayne Moore et al. and entitled "ACOUSTIC SYSTEM QUALITY ASSURANCE AND TESTING" U.S. patent application Ser. No. 12/536753 by G. Wayne Moore et al. and entitled "ACOUSTIC SYSTEM QUALITY ASSURANCE AND TESTING."

BACKGROUND OF THE INVENTION

This application relates generally to acoustic probes and systems. More specifically, this application relates to apparatus and methods for testing acoustic systems.

Acoustic imaging techniques have been found to be extremely valuable in a variety of applications. While medical applications in the form of ultrasound imaging are perhaps the most well known, acoustic techniques are more generally used at a variety of different acoustic frequencies for imaging a variety of different phenomena. For example, acoustic imaging techniques may be used for the identification of structural defects, for detection of impurities, as well as for the detection of tissue abnormalities in living bodies. All such techniques rely generally on the fact that different structures, whether they be cancerous lesions in a body or defects in an airplane wing, have different acoustic impedances. When acoustic radiation is incident on an acoustic interface, such as where the acoustic impedance changes discontinuously, it may be scattered in ways that permit characterization of the interface. Radiation reflected by the interface is most commonly detected in such applications, but transmitted radiation is also used for such analysis in some applications.

Transmission of the acoustic radiation towards a target and receipt of the scattered radiation may be performed and/or coordinated with a modern acoustic imaging system. Many modern such systems are based on multiple-element array transducers that may have linear, curved-linear, phased-array, or similar characteristics. These transducers may, for example, form part of an acoustic probe. In some instances, the imaging systems are equipped with internal self-diagnostic capabilities that allow limited verification of system operation, but do not generally provide effective diagnosis of the transmission and receiving elements themselves. Degradation in performance of these elements is often subtle and occurs as a result of extended transducer use and/or through user abuse. Acoustic imaging devices therefore often lack any direct quantitative method for evaluating either system or probe performance. Users and technical support personnel thus sometimes use phantoms that mimic characteristics of the object under study to provide a qualitative method for evaluating image quality and to perform a differential diagnosis between the system and the transducer array, but this technique is widely recognized to be of limited utility.

There is, therefore, a general need in the art for apparatus and methods for testing acoustic probes and systems.

BRIEF SUMMARY OF THE INVENTION

Embodiments of the invention provide systems and methods for testing acoustic systems. According to one embodiment, a method for testing an acoustic system can comprise receiving a signal from the acoustic system at a testing device coupled with the acoustic system via one of a plurality of channels between the acoustic system and the testing device. The signal can include a pattern of pulses. At least one pulse from the pattern pulses of the signal can be detected with the testing device. Detecting the at least one pulse can comprise matching the pattern of pulses to an expected pulse pattern for the acoustic system. A response to the signal from the acoustic system can be provided by generating an echo pulse with the testing device based on the detected at least one pulse wherein the echo pulse mimics a response to the detected at least one pulse for a selected acoustic probe For example, matching the pattern of pulses to an expected pulse pattern for the acoustic system can comprise determining whether the pulse pattern includes a first pulse type. In response to determining the pulse pattern includes the first pulse type, a determination can be made as to whether the pulse pattern further includes a second pulse type. In response to determining the pulse pattern further includes the second pulse type a subsequent pulse of the second pulse type can be detected. Matching the pattern of pulses to an expected pulse pattern for a selected acoustic probe can be performed, for example, by a Deterministic Finite Automaton.

The first pulse type and the second pulse type can be distinguished based on a time between adjacent pulses. In some cases, prior to receiving the signal from the acoustic system, a selection of the selected acoustic probe can be received at the testing device, for example from a host computer. Receiving the selection of the selected acoustic probe can comprise receiving probe specific data for the selected acoustic probe and system specific data for the acoustic system. For example, the system specific data can include information indicating a time between adjacent pulses for the first pulse type and a time between adjacent pulses for the second pulse type. In such cases, matching the pattern of pulses to an expected pulse pattern for the acoustic system can be based on the system specific data.

According to another embodiment, a system for testing an acoustic system can include a testing device. The testing device can comprise an interface adapted to communicatively interface with a plurality of channels of the acoustic system and a switch matrix communicatively coupled with the interface. The switch matrix can be adapted to select one of the plurality of channels and receive a signal from the acoustic system via the selected one of a plurality of channels. The signal can include a pattern of pulses. A pulse detection module or the testing device can be communicatively coupled with the switch matrix and can be adapted to detect at least one pulse from the pattern pulses of the signal. The testing device can also include an echo pulse synthesizer communicatively coupled with the switch matrix and pulse detection module. The echo pulse synthesizer can be adapted to respond to the signal from the acoustic system by generating an echo pulse based on the detected at least one pulse wherein the echo pulse mimics a response to the detected at least one pulse for a selected acoustic probe.

A computational unit of the testing device can be communicatively coupled with the interface, switch matrix, pulse detection module, and echo pulse synthesizer. The computational unit can be adapted match the pattern of pulses to an expected pulse pattern for the acoustic system. For example, matching the pattern of pulses to an expected pulse pattern for the acoustic system can comprise determining whether the pulse pattern includes a first pulse type. In response to determining the pulse pattern includes the first pulse type, a determination can be made as to whether the pulse pattern further includes a second pulse type. The first pulse type and the second pulse type can be distinguished, for example, based on a time between adjacent pulses. In response to determining the pulse pattern further includes the second pulse type a subsequent pulse of the second pulse type can be detected. In some cases, matching the pattern of pulses to an expected pulse pattern for a selected acoustic probe is performed by a Deterministic Finite Automaton.

The system can further comprise a host computer communicatively coupled with the computational unit of the testing device. In such cases, prior to receiving the signal from the acoustic system, the computational unit can receive a selection of the selected acoustic probe. For example, receiving the selection of the selected acoustic probe can comprise receiving probe specific data for the selected acoustic probe and system specific data for the acoustic system. The system specific data can include, for example, information indicating a time between adjacent pulses for the first pulse type and a time between adjacent pulses for the second pulse type. In such cases, matching the pattern of pulses to an expected pulse pattern for the acoustic system is based on the system specific data.

According to yet another embodiment, a machine-readable medium can have stored thereon a series of instructions which, when executed by a processor, cause the processor to test an acoustic system by receiving a signal from the acoustic system at a testing device coupled with the acoustic system via one of a plurality of channels between the acoustic system and the testing device. The signal can include a pattern of pulses. At least one pulse from the pattern pulses of the signal can be detected with the testing device. Detecting the at least one pulse can comprise matching the pattern of pulses to an expected pulse pattern for the acoustic system. A response to the signal from the acoustic system can be provided by generating an echo pulse with the testing device based on the detected at least one pulse wherein the echo pulse mimics a response to the detected at least one pulse for a selected acoustic probe.

For example, matching the pattern of pulses to an expected pulse pattern for the acoustic system can comprise determining whether the pulse pattern includes a first pulse type. In response to determining the pulse pattern includes the first pulse type, a determination can be made as to whether the pulse pattern further includes a second pulse type. In response to determining the pulse pattern further includes the second pulse type a subsequent pulse of the second pulse type can be detected. Matching the pattern of pulses to an expected pulse pattern for a selected acoustic probe can be performed, for example, by a Deterministic Finite Automaton.

The first pulse type and the second pulse type can be distinguished based on a time between adjacent pulses. In some cases, prior to receiving the signal from the acoustic system, a selection of the selected acoustic probe can be received at the testing device, for example from a host computer. Receiving the selection of the selected acoustic probe can comprise receiving probe specific data for the selected acoustic probe and system specific data for the acoustic system. For example, the system specific data can include information indicating a time between adjacent pulses for the first pulse type and a time between adjacent pulses for the second pulse type. In such cases, matching the pattern of pulses to an expected pulse pattern for the acoustic system can be based on the system specific data.

DETAILED DESCRIPTION OF THE INVENTION

Figure 1:
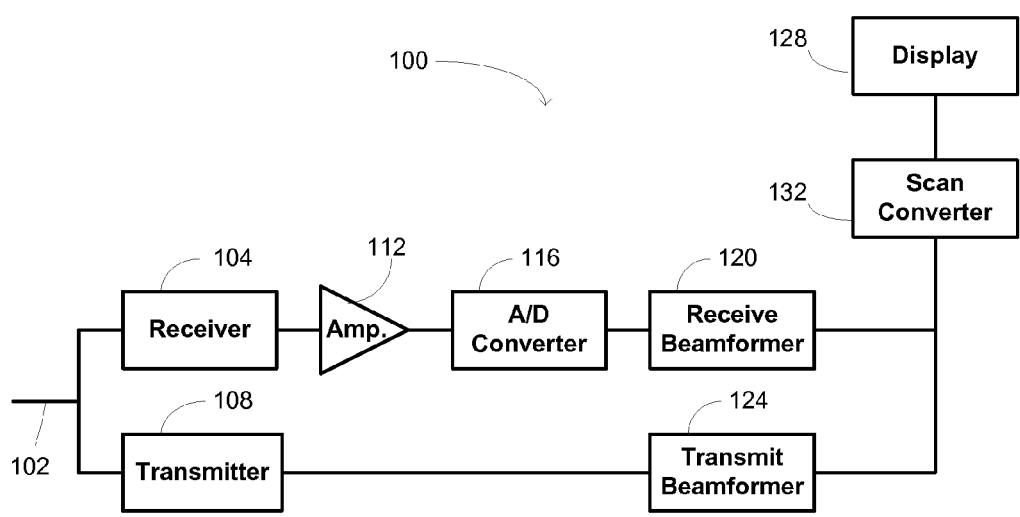
FIG. 1 is a block diagram illustrating an exemplary acoustic system that may be tested using various embodiments of the present invention.

In the following description, for the purposes of explanation, numerous specific details are set forth in order to provide a thorough understanding of various embodiments of the present invention. It will be apparent, however, to one skilled in the art that embodiments of the present invention may be practiced without some of these specific details. In other instances, well-known structures and devices are shown in block diagram form.

The ensuing description provides exemplary embodiments only, and is not intended to limit the scope, applicability, or configuration of the disclosure. Rather, the ensuing description of the exemplary embodiments will provide those skilled in the art with an enabling description for implementing an exemplary embodiment. It should be understood that various changes may be made in the function and arrangement of elements without departing from the spirit and scope of the invention as set forth in the appended claims.

Specific details are given in the following description to provide a thorough understanding of the embodiments. However, it will be understood by one of ordinary skill in the art that the embodiments may be practiced without these specific details. For example, circuits, systems, networks, processes, and other components may be shown as components in block diagram form in order not to obscure the embodiments in unnecessary detail. In other instances, well-known circuits, processes, algorithms, structures, and techniques may be shown without unnecessary detail in order to avoid obscuring the embodiments.

Also, it is noted that individual embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process is terminated when its operations are completed, but could have additional steps not included in a figure. A process may correspond to a method, a function, a procedure, a subroutine, a subprogram, etc. When a process corresponds to a function, its termination can correspond to a return of the function to the calling function or the main function.

The term "machine-readable medium" includes, but is not limited to portable or fixed storage devices, optical storage devices, wireless channels and various other mediums capable of storing, containing or carrying instruction(s) and/or data. A code segment or machine-executable instructions may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

Furthermore, embodiments may be implemented by hardware, software, firmware, middleware, microcode, hardware description languages, or any combination thereof. When implemented in software, firmware, middleware or microcode, the program code or code segments to perform the necessary tasks may be stored in a machine readable medium. A processor(s) may perform the necessary tasks.

Embodiments of the invention provide apparatus and methods for testing acoustic systems. While much of the discussion below specifically discusses apparatus and methods that are suitable for testing ultrasonic systems, this is intended merely for exemplary purposes and the invention is not intended to be limited by the operational frequency characteristics used by the tested system. Generally speaking, apparatus and methods described herein can be embodied, for example, in a testing device that can be connected to an acoustic system to be tested, for example via a port or receptacle through which an acoustic probe is typically connected to the acoustic system. As will be described in greater detail below, this testing device can be adapted to mimic any one of a number of different acoustic probes and can operate with and test a variety of different acoustic systems and functions thereof. Such a testing device can be used by medical device technical and service professionals to test, troubleshoot and objectively verify the performance of diagnostic acoustic systems.

As described in greater detail below, each of the acoustic systems that may be tested with embodiments of the invention includes a plurality of elements adapted to transmit signals to an acoustic probe and to receive a response or echo signal from the acoustic probe. Reference is sometimes made herein to "receiver elements" and to "transmitter elements" to distinguish the elements of the acoustic system and the testing device on the basis of their functions. Embodiments of the invention diagnose operation of the acoustic system using the testing device connected with the acoustic system and adapted to use electro-acoustic signal injection techniques described below to generate an echo signal and return the echo signal to the acoustic system to mimic a selected acoustic probe.

More specifically, testing of an acoustic system in embodiments of the invention may be performed with a switch matrix of the testing device for selectively establishing operational connections with channels comprised by the acoustic system. Connections may be established sequentially with the channels, either individually or in groups. This permits evaluation of a transmitter circuit comprised by the acoustic system as it is connected through each channel. In addition, scattering operations of a particular probe may be simulated electrically for each channel by transmission of the echo signal through the sequential connections. According to embodiments of the present invention, these scattering operations can be simulated for one of any number of possible probes based on a type of probe selected by the user and as expected by the acoustic system under test. More specifically, a signal transmitted to the testing device by the acoustic system can be evaluated to identify a mode of operation of the acoustic system for which the signals are transmitted. Based on the type of probe selected and the identified transmitted signal from the acoustic system, an appropriate echo signal can be generated and returned to the acoustic system through the sequential connections established by the switch matrix. Operation of a receiver circuit comprised by the acoustic system may thus be evaluated through evaluation of image data produced by the acoustic system in response to the simulated scattering operations.

Stated another way, testing an acoustic system can comprise receiving a signal from the acoustic system at a testing device coupled with the acoustic system via one of a plurality of channels between the acoustic system and the testing device. The signal can include a pattern of pulses. In some cases, the pulses can include Doppler pulses. At least one pulse from the pattern of pulses of the signal can be detected with the testing device. Detecting the at least one pulse can comprise matching the pattern of pulses to an expected pulse pattern for the acoustic system. For example, matching the pattern of pulses to an expected pulse pattern for the acoustic system can comprise determining whether the pulse pattern includes a first pulse type. In response to determining the pulse pattern includes the first pulse type, a determination can be made as to whether the pulse pattern further includes a second pulse type. In response to determining the pulse pattern further includes the second pulse type a subsequent pulse of the second pulse type can be detected. Matching the pattern of pulses to an expected pulse pattern for a selected acoustic probe can be performed, for example, by a Deterministic Finite Automaton.

The first pulse type and the second pulse type can be distinguished based on a time between adjacent pulses. In some cases, prior to receiving the signal from the acoustic system, a selection of the selected acoustic probe can be received at the testing device, for example from a host computer. Receiving the selection of the selected acoustic probe can comprise receiving probe specific data for the selected acoustic probe and/or system specific data for the acoustic system. For example, the system specific data can include information indicating a time between adjacent pulses for the first pulse type and a time between adjacent pulses for the second pulse type. In such cases, matching the pattern of pulses to an expected pulse pattern for the acoustic system can be based on the system specific data. It should be noted that while described here with reference to two pulse types for the sake of clarity and brevity, embodiments of the present invention are not limited to only two pulse types. Rather, any number of pulse types may be handled. For example, a Color Doppler signal may use six or more pulse types. Depending upon the exact implementation of the state machine, any or all of these pulse types may be captured. All such implementations are considered to be within the scope of the present invention.

A response to the signal from the acoustic system can be provided by generating an echo pulse with the testing device based on the detected at least one pulse. The echo pulse can mimic a response to the detected at least one pulse for a selected acoustic probe. In the case of Doppler pulses, the echo pulse is frequency shifted from the detected at least one Doppler pulse and mimics a response to the detected at least one Doppler pulse for a selected acoustic probe. For example, generating the echo pulse for a Doppler pulse can comprise determining a frequency of the detected at least one Doppler pulse. Pulses of a clock having a frequency higher than the frequency of the detected at least one Doppler pulse can be accumulated. The accumulated pulses can be output when the accumulated pulses reach a pre-determined threshold. Accumulating pulses of the clock and outputting the accumulated pulses can be repeated.

As noted above, prior to receiving the signal from the acoustic system, a selection of the selected acoustic probe can be received at the testing device, for example from a host computer. Receiving the selection of the selected acoustic probe can also comprise receiving probe specific data for the selected acoustic probe. In such cases, generating the echo pulse can be based at least in part on the probe specific data. In some cases, user selected response parameters can also be received at the testing device. Such parameters can include but are not limited to amplitudes for the echo pulses, depth within the image, location along an image vector line, etc. In such cases, generating the echo pulse can be further based on the user selected response parameters.

Performance of the acoustic system can be analyzed with the testing device based on the detected at least one pulse. For example, analyzing performance of the acoustic system with the testing device can comprise capturing at least one pulse from the plurality of pulses of the signal. In some cases, the captured pulse(s) can be saved, for example in memory of the testing device. Additionally or alternatively, analyzing performance of the acoustic system with the testing device can comprise providing the captured at least one pulse from the testing device to a host computer. In such cases, one or more analysis tools can be applied to the captured at least one pulse with the host computer. Additionally or alternatively, the host computer can display the captured at least one pulse. Various additional details of embodiments of the present invention will be described below with reference to the figures.

FIG. 1 is a block diagram representation of an exemplary acoustic system that may be tested using various embodiments of the present invention. It should be noted and will be evident to those of skill in the art after reading this description that the methods and apparatus of the invention may alternatively be used for operational diagnosis of other types of acoustic systems. The components shown for the acoustic system structure in FIG. 1 are shared by a large number of different acoustic systems, although specific systems may have these components organized differently.

The acoustic system 100 includes a multichannel interface 102 that is in communication with receiver 104 and transmitter 108 components. The receiver 104 and transmitter 108 are configured for conversion between electrical and acoustic signals so that investigation of an object may be performed by irradiating the object with the acoustic signals but performing analysis with the electrical signals. Thus, the receiver 104 may include components that convert acoustic signals to electrical signals while the transmitter 108 may conversely include components that convert electrical signals to acoustic signals. Generally, each of the receiver 104 and transmitter 108 are configured with multichannel capacity. The receiver 104 may be provided in communication with an amplifier 112 and analog-to-digital converter 116 to accommodate acoustic signals that may be attenuated after scattering by the object by amplifying and digitizing the converted electrical signals. Thus, after digitization, differences between the received and transmitted electrical signals provide information derived from scattering of the corresponding acoustic signals from the object.

The multichannel information provided from the multichannel interface 102 is accommodated by a receive beamformer 120 and a transmit beamformer 124, each of which is respectively configured for adding contributions from a plurality of elements comprised by the receiver and transmitter elements 104 and 108. The receive and transmit beamformers 120 and 124 include array phasing capability to be applied respectively for the received and transmitted signals. The acoustic system 100 may include a capacity for displaying an image, which is typically viewed by an operator trained in evaluating acoustic images so that features of interest in the object, such as medical pathologies in an organ, may be identified. The image is generated by a scan converter 132 provided in communication with the receive and transmit beamformers 120 and 124 and transmitted to a display 128 for rendering.

The testing methods and apparatus provided by embodiments of the invention may be used to diagnose the operational behavior of acoustic systems such as that described in connection with FIG. 1. In particular, embodiments of the invention permit defects to be identified in the operation of individual receiver and transmitter elements. Such defects are often not immediately apparent in the image provided on the display 128 because the image is derived from multiple elements. Nevertheless, the absence of information from a defective element may result in subtle distortions of the image that may lead to incorrect analyses of the object under study.

As noted above, embodiments of the invention provide apparatus and methods for testing acoustic systems such as acoustic system 100. Also as noted above, the acoustic system 100 tested can be any of a variety of possible acoustic systems. According to one embodiment the acoustic system can comprise a system used for testing acoustic probes such as the FirstCall aPerio™ system provided by Sonora Medical Systems, Inc. of Longmont, Colo. Such a system is described, for example, in commonly assigned U.S. Pat. No. 7,028,529 which is incorporated herein by reference for all purposes. Regardless of the exact type of acoustic system tested, embodiments of the present invention can comprise a testing device that can be connected to an acoustic system to be tested, for example via a multichannel interface 102 through which an acoustic probe is typically connected to the acoustic system 100.

Figure 2:
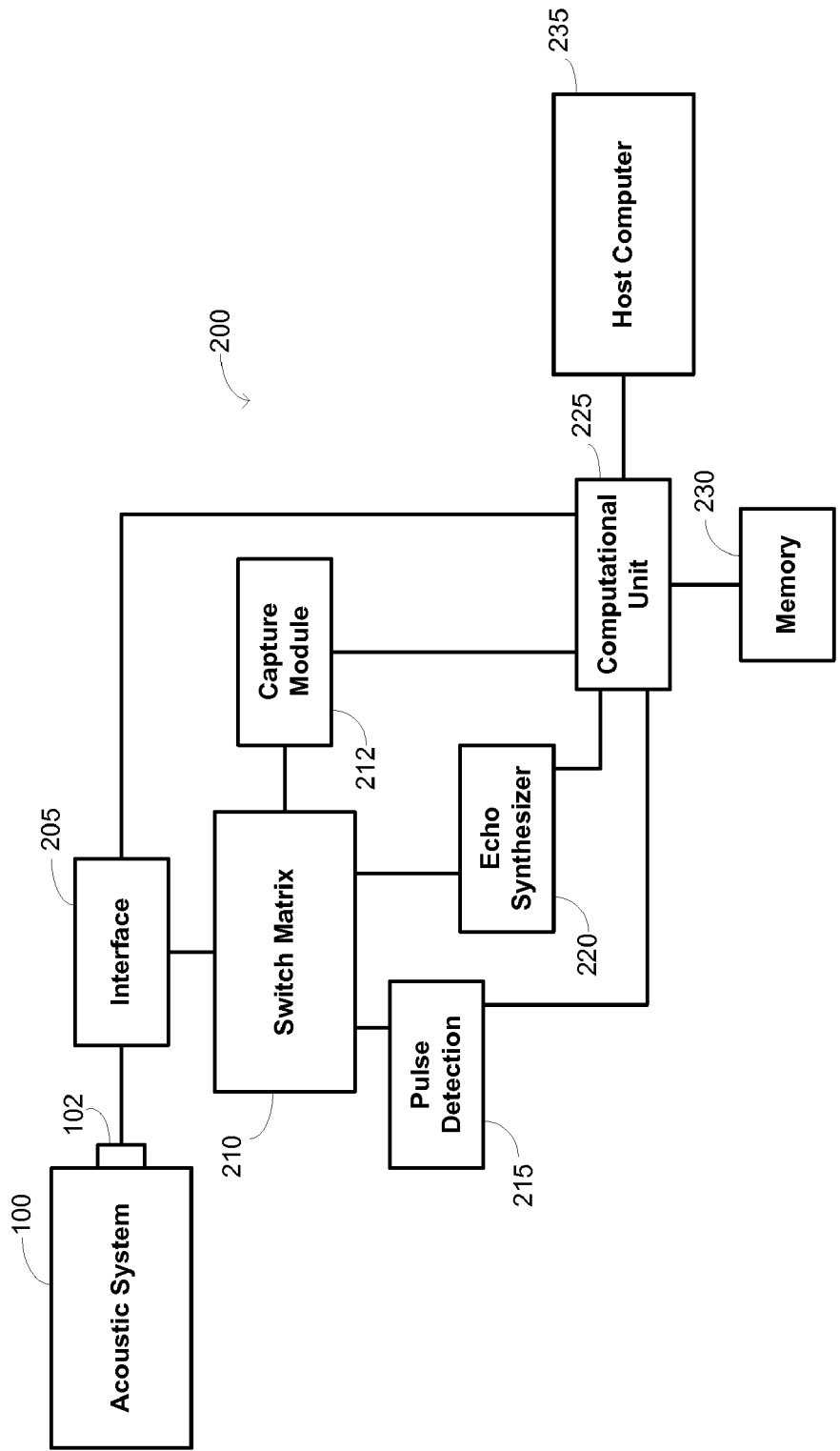
FIG. 2 is a block diagram illustrating elements of a device for testing an acoustic system according to one embodiment of the present invention.

FIG. 2 is a block diagram illustrating elements of a device for testing an acoustic system according to one embodiment of the present invention. Illustrated here are the acoustic system 100 and multichannel interface 102 of the acoustic system 100 as described above. The device 200 for testing the acoustic system 100 can include an interface 205 adapted to be communicatively coupled with the multichannel interface 102 of the acoustic system 100. The testing device 200 can also comprise a switch matrix 210 communicatively coupled with the interface 205. The switch matrix 210 can be adapted to select one of the plurality of channels of the multichannel interface 102 of the acoustic system 100 and receive a signal from the acoustic system 100 via the selected one of a plurality of channels.

The switch matrix 210 can be adapted to perform signal mapping from one channel to a plurality of channels in communication with the interface 205. In one embodiment, the natural cycling of the acoustic system 100 through its multiple channels is used to evaluate operation of transmitter elements. Signals generated by elements of the acoustic system 100 are collected by the switch matrix 210 through the interface 205. The switch matrix 210 can be configured for discrimination of individual channels received from the acoustic system 100 through the interface 205. In another embodiment, operation of the receiver elements of the acoustic system 100 may be evaluated by providing synthesized echo pulses back into the acoustic system 100 through the switch matrix 210 and interface 205 as will be described below.

A pulse detection module 215 of the testing device can be communicatively coupled with the switch matrix 210 and can be adapted to detect at least one pulse from a pattern of pulses of the signal. The testing device 200 can also include an echo pulse synthesizer 220 communicatively coupled with the switch matrix 210 and pulse detection module 215 and can be adapted to respond to the signal from the acoustic system 100 by generating an echo pulse based on the detected at least one pulse wherein the echo pulse mimics a response to the detected at least one pulse for a selected acoustic probe. That is, in response to a signal received from the acoustic system 100 through the interface 205 and switch matrix 210, the pulse detection module 215 can identify one or more pulses in the signal and activate the echo synthesizer 220, which in turn generates an echo pulse to be routed back into the acoustic system 100. Specific channels corresponding to different elements are selected according to a configuration of the switch matrix 210 and the echo pulse output from the switch matrix 210 is transmitted to the acoustic system 100. In this way, the echo pulse is directed to a specific element of the acoustic system 100, causing a dot to be displayed on the display of the system 100 for each beam that that element is used on. A defective channel may thus be characterized by the absence of an expected line on the display. Such absence may be identified by a human operator, although in other embodiments a frame-capture device can be interfaced with the video output to detect the presence or absence of lines automatically. The switch matrix 210 may be cycled through each of the channels corresponding to all elements comprised by the acoustic system 100 to evaluate the operation of each of those elements.

The testing device 200 can further comprise a computational unit 225 communicatively coupled with the interface 205, switch matrix 210, pulse detection module 215, and echo pulse synthesizer 220. The computational unit 225 can be adapted to interact with and coordinate or control operation of the interface 205, switch matrix 210, pulse detection module 215, and echo pulse synthesizer 220. For example and according to one embodiment, a host computer 235 can be communicatively coupled with the computational unit 225, e.g., via a Universal Serial Bus (USB) or other serial or parallel connection. In such cases, the computational unit 225 can receive selection of the acoustic probe mimic, probe specific data for the selected acoustic probe, system specific data for the acoustic system being tested, and/or user selected response parameters from the host computer. It should be noted that, while referred to herein as a host computer, this name should not be considered to imply any limitations on the type of machine used or the functions performed thereby. For example, the host computer 235 need not be a server. Rather, in one implementation, the host computer may comprise a laptop, notebook, or tablet computer used by a technician performing the tests. In another embodiment, the host computer 235 may be implemented on a handheld device such as a Personal Digital Assistant (PDA) or other computing device.

Regardless of the exact form of the host computer 235, the computational unit 225 can be adapted to receive from the host computer 235 a selection of a selected acoustic probe to mimic including probe specific data for the selected acoustic probe and/or system specific data for the acoustic system 100 to be tested. For example, this information can be downloaded from the host computer 235 which previously obtained and saved the data, e.g., from a website or other facility of a manufacturer of the acoustic system, acoustic probe, or test device or from another service or entity. The computational unit 225 can then control the pulse detection module 215 and echo pulse synthesizer 220 to detect pulses within the input signal and generate the echo pulse(s) based at least in part on the probe specific data and/or system specific data. That is, the computational unit 225 can receive data from the host computer 235 describing the pulse types, the expected pattern which determines when operations are to be performed, and the operation(s) to perform. The computational unit 225 then applies the expected pattern to the pulses from the signal detected by the pulse detection module 215 and instructs the echo synthesizer 230 to generate an echo pulse based on the information received from the host computer 235. In some cases, the information can be received from the host computer on a continuous basis through out the test process, e.g., before each capture and response sequence.

Additionally or alternatively, the computational unit 225 can be adapted to receive user selected response parameters and control the echo pulse synthesizer 220 to generate the echo pulse further based on the user selected response parameters. For example, the user selected response parameters can include but are not limited to amplitudes for the echo pulses, depth within the image, location along an image vector line, etc. provided through the host computer 235 by a technician or other operator performing the tests.

According to one embodiment, the computational unit can be adapted match the pattern of pulses to an expected pulse pattern for the acoustic system. For example, matching the pattern of pulses to an expected pulse pattern for the acoustic system can comprise determining whether the pulse pattern includes particular pulse types. According to one embodiment, the pulse types can be distinguished based on a time between adjacent pulses. This time, and possibly other system specific information, for identifying pulse types can be provided to the computational unit 225 of the testing device 200 by the host computer 235 and saved in memory 230 of the testing device 200. Details of an exemplary process for performing such pattern matching will be described below with reference to FIGS. 7 and 8.

Generally speaking, the pulse detection module 215 can compare the input signal to a threshold. When the signal exceeds this threshold, other modules are notified that a pulse was detected. Anything that does not exceed the threshold, even if it is a real pulse output by the acoustic system, is not detected. Therefore, according to one embodiment, the pattern matching process described here may be applied to the pattern of pulses detected by the pulse detector rather than the pulses output by the acoustic system. In some cases, this threshold may be a fixed threshold. However, the amplitude of the signal output by a particular type of acoustic system is not necessarily the same system to system and the pattern of detected pulses may vary in unexpected ways system-to-system. Therefore, according to one embodiment, the threshold may be adjustable, i.e., the threshold can be tuned to a particular signal. Thus, the pattern matching process, e.g., using an appropriate state machine as will be described below with reference to FIG. 7, can detect certain conditions including but not limited to the presence or absence of a particular pulse type, the absence of any pulses whatsoever, the number of occurrences of a particular pulse type, the number of blocks of alternating pulse types, etc. Based on conditions programmed into the state machine, the threshold can be increased or reduced. In this way, a threshold that results in the expected pulse pattern can be determined, even for varying signal amplitudes. Additionally, this adjustable threshold provides an additional mechanism to discard pulses with a lower amplitude. By isolating the pulses of interest (i.e. those of greater amplitude), conditions under which a capture is initiated can be simplified.

In some cases and as noted above, the signal from the acoustic system 100 may include Doppler pulses. According to one embodiment, the echo pulse synthesizer 220 of the testing device 200 can be adapted to detect one or more Doppler pulses and respond to the signal from the acoustic system 100 by generating an echo pulse based on the detected at least one Doppler pulse. The echo pulse can be frequency shifted from the detected Doppler pulse(s) and can mimic a response to the captured Doppler pulse(s) for a selected acoustic probe. Details of an exemplary process for responding to Doppler pulses will be described below with reference to FIG. 9.

According to one embodiment, performance of the acoustic system 100 can be analyzed with the testing device 200 based on captured pulse(s). For example, the testing device 200 can also comprise a capture module 212 communicatively coupled with the switch matrix 210 and the computational unit 225. The capture module 212 can be adapted to capture at least one pulse from the plurality of pulses of the signal. The capture module 212 can be implemented, for example, as an A/D converter, a FIFO buffer, and software executed by the computational unit 225. As an alternative to software executed by the computational unit 225, the capture module 212 may be implemented using an ASIC. According to one embodiment, the capture module 212 and/or computational unit 225 can capture pulses based on information provided to the testing device 200 from the host computer 235, for example, indicating timing or other information for beginning of sampling the input signal.

Regardless of the exact implementation, the computational unit 225 of the testing device 200 can save the captured pulse(s) in memory 230 of the testing device 200. Additionally or alternatively, analyzing performance of the acoustic system 100 with the testing device 200 can comprise providing the captured pulse(s) from the testing device 200 to the host computer 235 for further analysis. The captured pulses may be provided to the host computer 235 in real time or can be provided from memory 230 for pulses captured previously. Analysis by the host computer 235 may be performed in real time and/or the captured pulses can be saved by the host computer 235 for analysis at a later time. For example, one or more analysis tools can be applied to the with the host computer 235 captured pulse(s) when or as provided by the testing device 200 or can be applied to saved pulses from previous tests. Additionally or alternatively, the host computer 235 can display the captured pulse(s) for interpretation by an operator or user.

Stated another way, testing of an acoustic system 100 in embodiments of the invention may be performed with a switch matrix 210 of the testing device 200 for selectively establishing operational connections with channels comprised by the acoustic system 100. Connections may be established sequentially with the channels, either individually or in groups. This permits evaluation of a transmitter circuit comprised by the acoustic system 100 as it is connected through each channel. In addition, scattering operations of a particular probe may be simulated electrically by the testing device 200 for each channel by transmission of the echo signal through the sequential connections. According to embodiments of the present invention, these scattering operations can be simulated for one of any number of possible probes based on a type of probe selected by the user, e.g., via host computer 235, and as expected by the acoustic system 100 under test. More specifically, a signal transmitted to the testing device 200 by the acoustic system 100 can be evaluated to identify a mode of operation of the acoustic system 100 for which the signals are transmitted. Based on the type of probe selected and the identified transmitted signal from the acoustic system 100, an appropriate echo signal can be generated by the echo pulse synthesizer 220 and returned to the acoustic system 100 through the sequential connections established by the switch matrix 210. Operation of a receiver circuit comprised by the acoustic system 100 may thus be evaluated through evaluation of image data produced by the acoustic system 100 in response to the simulated scattering operations.

The electro-acoustic signal injection techniques implemented in embodiments of the present invention and described herein provide the ability to input discrete signals of a wide range of amplitude into the front-end electronics of the acoustic system 100 under test. The signals can be processed by the acoustic system 100 and displayed in a manner consistent with a returning signal of the acoustic probe selected and mimicked by the testing device 200. By using this approach the testing device 200 can measure, among other performance parameters, the Local Dynamic Range (LDR) of the acoustic system 100. Via the host computer 235 and testing device 200, the operator can select among a range of signal amplitudes that can be injected at various depths within the image and along various imaging vector lines, thereby allowing the operator to establish a "baseline" of performance for the specific acoustic system 100 against which future measurements can be compared to ensure quality imaging.

According to one embodiment, the testing device 200 can be adapted to detect the transmit pulses from the acoustic system 100 in various modes, e.g., B-mode, M-mode, Spectral Doppler and Color Flow. As noted above, the testing device 200 can receive and respond to Doppler signals and allow the operator to select a specific velocity and Doppler signal amplitude. This makes it possible to establish a performance baseline for this modality on a given acoustic system, thereby providing an objective measure of the Doppler accuracy and sensitivity. Similarly, color flow signals received and responded to by the testing device 200 test the sensitivity of the color flow mode of the acoustic system 100 as well as color flow registration and velocity accuracy. With the ability to mimic sub-apertures of an array or an acoustic probe, the testing device 200 can additionally or alternatively test special image processing functions of the acoustic system such as spatial compounding. According to one embodiment, individual sector lines of the acoustic system 100 can be illuminated and pixels along that line can be addressed. This allows the operator to use the testing device 200 to test the accuracy of the acoustic system's electronic calipers in both the axial and lateral dimensions. According to one embodiment, imaging processing software resident within the host computer 235 can then analyze the displayed signals on the acoustic system monitor via a frame-grabber option.

Figure 3:
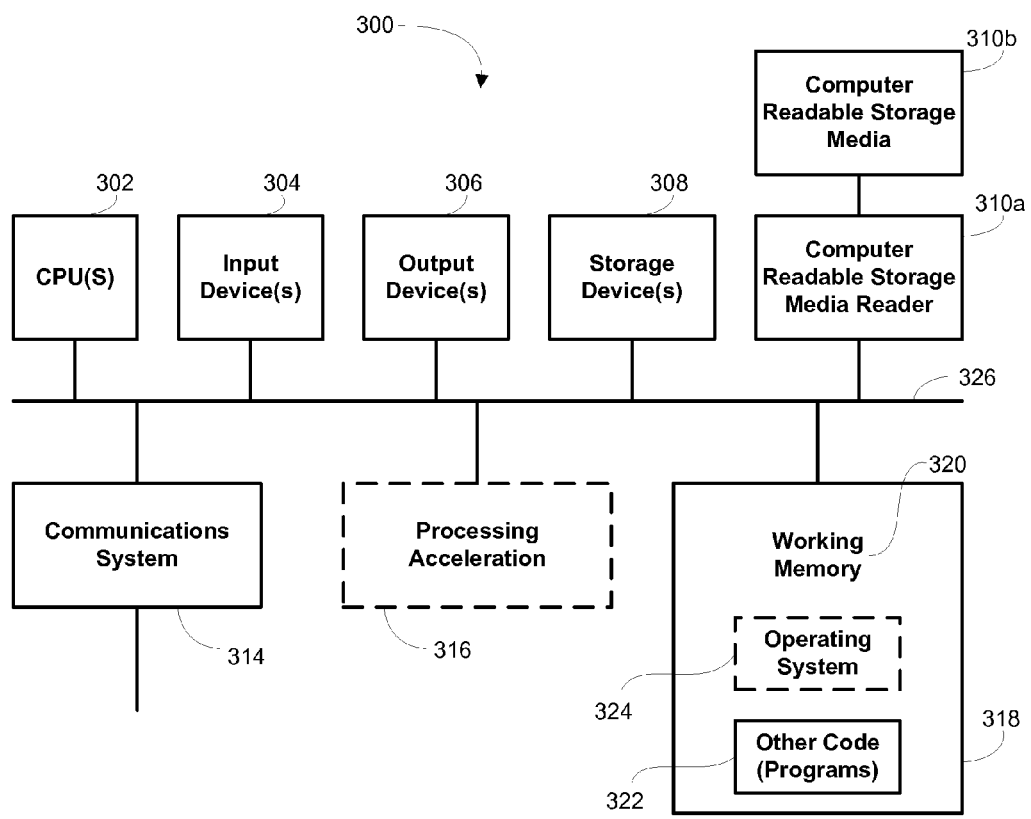
FIG. 3 is a block diagram illustrating a computational unit on which embodiments of the present invention may be implemented.

FIG. 3 is a block diagram illustrating a computational unit on which embodiments of the present invention may be implemented. This example illustrates a system 300 that can be used, in whole or in part or in combination with other elements not shown here to implement the acoustic system 100, computational unit 225 of the testing device 200 and/or the host computer 235 described above. The system 300 is shown comprised of hardware elements that are electrically coupled via bus 326, including a processor 302, an input device 304, an output device 306, a storage device 308, a computer-readable storage media reader 310a, a communications system 314, a processing acceleration unit 316 such as a DSP or special-purpose processor, and a memory 318. The computer-readable storage media reader 310a is further connected to a computer-readable storage medium 310b, the combination comprehensively representing remote, local, fixed, and/or removable storage devices plus storage media for temporarily and/or more permanently containing computer-readable information. The communications system 314 may comprise a wired, wireless, modem, and/or other type of interfacing connection and permits data to be exchanged with external devices as desired.

The system 300 also comprises software elements, shown as being currently located within working memory 320, including by way of example but not limited to an operating system 324 and other code 322, such as a program designed to implement methods of the invention. It should be understood that operating system 324 can be considered optional and in some implementations code such as machine code implementing embodiments of the present invention can be executed directly by CPU 302 without reliance on an operating system. It will be apparent to those skilled in the art that substantial other variations may be made in accordance with specific requirements. For example, customized hardware might also be used and/or particular elements might be implemented in hardware, software (including portable software, such as applets), or both. Further, connection to other computing devices such as network input/output devices may be employed. Connections between the computational unit 132 and the various components of the testing apparatus may use any suitable connection, such as a parallel-port connection, a universal-serial-bus ("USB") connection, and the like.

Figure 4:
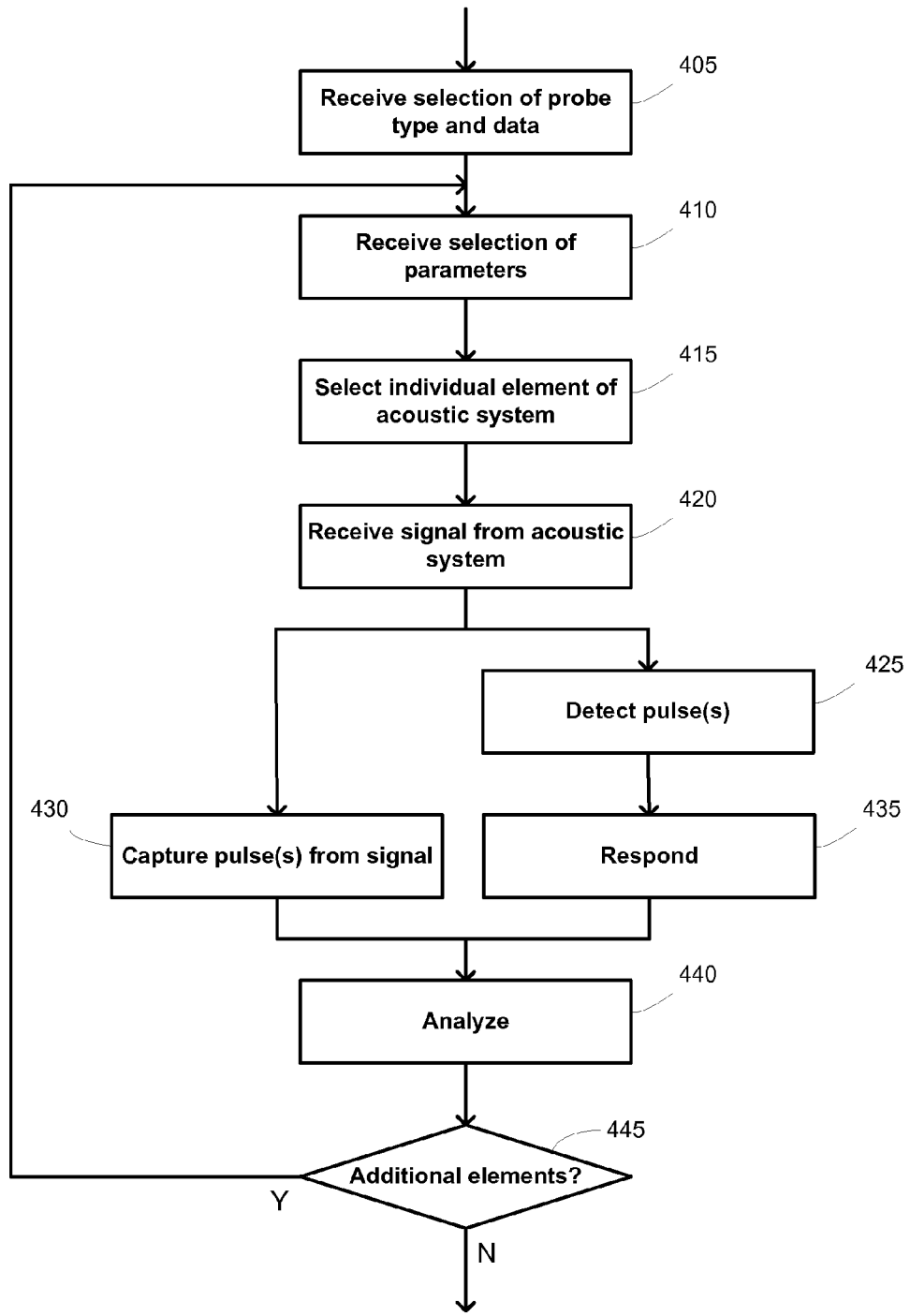
FIG. 4 is a flowchart illustrating a process for testing an acoustic system according to one embodiment of the present invention.

FIG. 4 is a flowchart illustrating a process for testing an acoustic system according to one embodiment of the present invention. In this example, processing begins with receiving 405 a selection of an acoustic probe to be mimicked. Receiving 405 the selection of the selected acoustic probe can also comprise receiving probe specific data for the selected acoustic probe. As noted above, this selection can be made, for example, via the host computer by accessing or selecting information and/or settings for a particular probe previously stored in memory of the testing device or by downloading such information and/or settings from the host computer to the testing device. As also described above, any number and variety of user selected parameters can also be received 410. That is, user parameters for performing a test of the acoustic system such as amplitudes for the echo pulses, depth within the image, location along an image vector line, etc. can be received 410 at the testing device from the host computer.

One of the plurality of channels can be selected 415, e.g., via the switch matrix described above. A signal can be received 420 from the acoustic system at a testing device coupled with the acoustic system. As noted above, the signal can include a pattern of pulses received 420 via the selected channel between the acoustic system and the testing device. At least one pulse from the pattern of pulses of the signal on the selected channel can be detected 425 with the testing device. As noted above, detecting 425 pulses from a pattern of pulses can include performing a pattern matching process based on system specific information. An exemplary process for performing such pattern matching is described in greater detail below with reference to FIGS. 7 and 8.

Once one or more pulses have been detected 425, a response to the signal from the acoustic system can be provided 430 by generating an echo pulse with the testing device based on the detected pulse(s) and information from the host computer. The echo pulse can mimic a response to the detected pulse(s) for the selected acoustic probe. Thus, generating the echo pulse can be based on one or more of probe specific information for the probe being mimicked, system specific information for the system being tested, and/or user specified parameters for the response. As noted above, the detected pulse(s) may, in some cases, include Doppler pulses. An exemplary process for generating echo pulses for Doppler pulses is described in greater detail below with reference to FIG. 9.

According to one embodiment, one or more pulses from the plurality of pulses of the signal can also be captured 430 by the testing device. Capturing 430 one or more pulses can comprise sampling a section of an input signal, storing the sample in memory of the device, and possibly providing the captured pulse(s) to the host computer. It should be understood that while illustrated here as a parallel process to detecting 425 and responding 430 to a pulse, capturing 430 pulses need not be performed in parallel or concurrently in other implementations. In any case, once one or more pulses have been captured 430, performance of the acoustic system can be analyzed 440 with the testing device based on the captured pulse(s). For example, analyzing 440 performance of the acoustic system with the testing device can comprise saving the captured pulse(s). Additionally or alternatively, analyzing 440 performance of the acoustic system with the testing device can comprise providing the captured pulse(s) from the testing device to the host computer for further analysis in real time or at a later time. For example, one or more analysis tools can be applied to the captured pulse(s) with the host computer. Additionally or alternatively, the host computer can display the captured pulse(s) for interpretation by an operator or user.

A determination 445 can be made as to whether to continue testing. For example, this determination 445 can be based on whether other elements of channels of the interface with the acoustic system remain to be tested. If 445 additional channels remain to be tested, processing can return to receive 410 selection of parameters, select 415 another channel, receive 420 a signal via the selected channel, detect 425 and respond 430 to pulses of the signal, capture 430 pulse(s) from the signal on the selected channel, and analyze 440 the signal. This process can be repeated until all channels of the interface with the acoustic system have been tested or the test is otherwise stopped or suspended.

Figure 5:
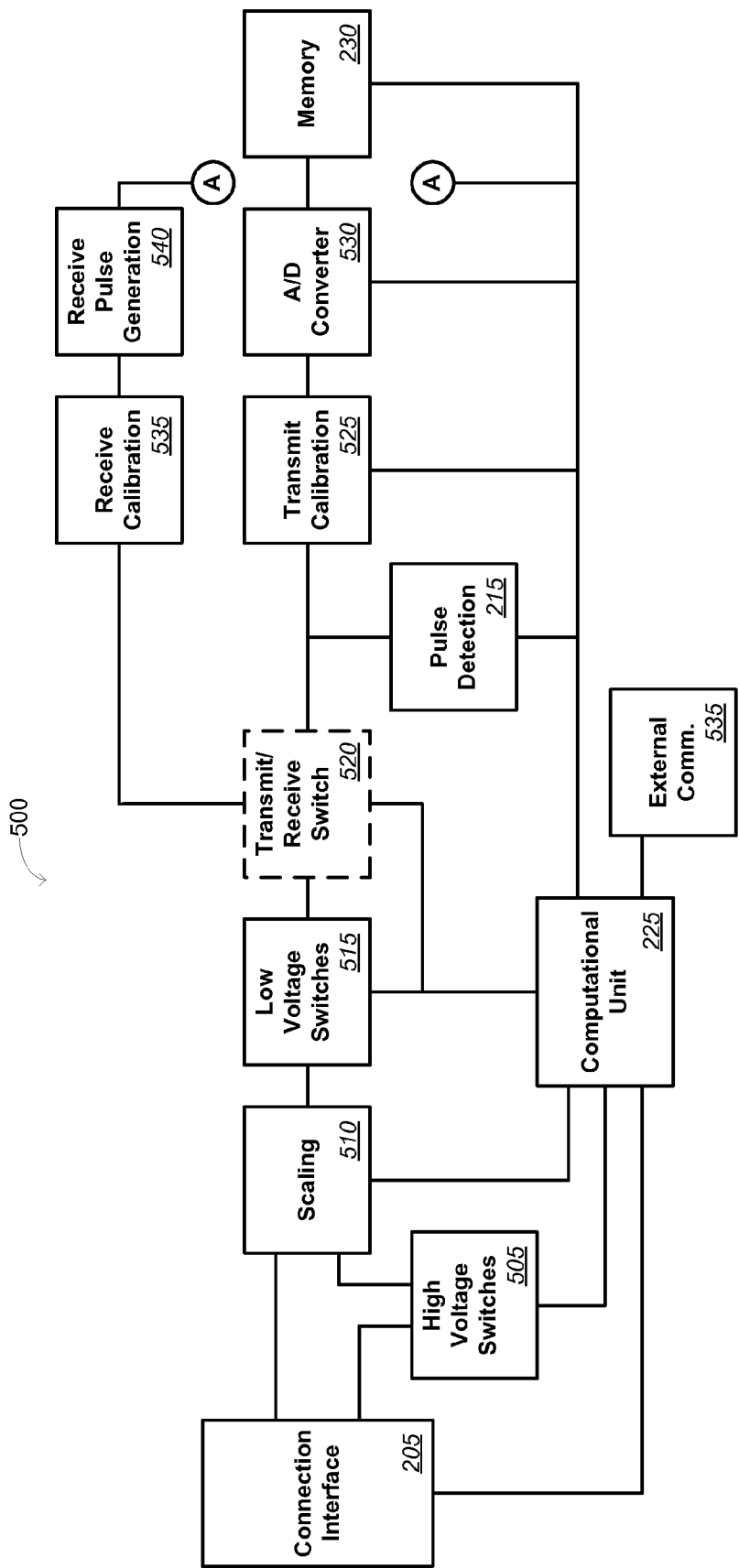
FIG. 5 is a block diagram illustrating additional details of elements of a device for testing acoustic systems according to one embodiment of the present invention.

FIG. 5 is a block diagram illustrating additional details of elements of a device for testing acoustic systems according to one embodiment of the present invention. Similar to the example described above with reference to FIG. 2, the device 500 illustrated here for testing an acoustic system can include an interface 205 adapted to be communicatively coupled with a multichannel interface of the acoustic system. As noted above, the testing device 500 can also comprise a switch matrix communicatively coupled with the interface 205. As illustrated here, the switch matrix can include a matrix of high voltage switches 505 as well as a matrix of low voltage switches 515. To allow the low voltage switches to accept voltages provided by the acoustic system, a scaling module, implemented for example as a resistive potential divider, can be provided between he connection interface 205 and the low voltage switches 515. The switch matrix of the test device 500 can also include a transmit/receive switch 520 for switching the testing device 500 between operations of receiving pulses from the acoustic system and transmitting echo pulses back to the acoustic system. However, in other implementations, rather than using the transmit/receive switches 520, the pulse detection module 215, transmit calibration module 525 and receive calibration module 535 may be connected to the low voltage switches 515. As described above, the switch matrix, i.e., the high voltage switches 505, low voltage switches 515 with scaling module 510, and transmit/receive switch 520 (if used), can be adapted to select one of the plurality of channels of the multichannel interface of the acoustic system and receive a signal from the acoustic system via the selected one of a plurality of channels through the interface 205.

As described previously, a pulse detection module 215 of the testing device can be communicatively coupled with the switch matrix via transmit/receive switch 520 and can be adapted to detect at least one pulse from a pattern of pulses of the signal. Pulse detection functions of the pulse detection module can be supported by transmit calibration module 525 and a/d converter 530. The testing device 500 can also include an echo pulse synthesizer communicatively coupled with the switch matrix via transmit receive switch 520. As illustrated in this example, the echo synthesizer can include a receive pulse generation module 540 and receive pulse calibration module 535. The receive pulse generation module 540 and receive pulse calibration module 535 can be adapted to respond to the signal from the acoustic system by generating an echo pulse based on the captured at least one pulse wherein the echo pulse mimics a response to the detected at least one pulse for a selected acoustic probe. That is, in response to a signal received from the acoustic system through the interface 205 and switch matrix, i.e., the high voltage switches 505, low voltage switches 515 with scaling module 510, and transmit/receive switch 520, the pulse detection module 215 can identify one or more pulses in the signal and activate the receive pulse generation module 540, which in turn generates an echo pulse to be routed back into the acoustic system.

The testing device 500 can further comprise a computational unit 225 communicatively coupled with the other elements of the testing device 500. The computational unit 225 can be adapted to interact with and coordinate or control operation of the elements of the testing device 500. For example and according to one embodiment, a host computer can be communicatively coupled with the computational unit 225, e.g., via an external communications module 535 such as a Universal Serial Bus (USB) or other serial or parallel connection. In such cases, the computational unit 225 can receive selection of the acoustic probe mimic, probe specific data for the selected acoustic probe, system specific data for the acoustic system being tested, and/or user selected response parameters from the host computer. Generally speaking, the computational unit can perform operations such as described above, e.g., detecting pulses based on a pattern matching process, responding to the captured pulses, including possibly Doppler pulses, etc. For example, to respond to Doppler pulses, the receive pulse generation module can comprise a clock having a frequency higher than a frequency of the captured Doppler pulse(s). An accumulator, e.g., in memory 230, can be adapted to accumulate pulses of the clock. The computational unit 225 can then output the accumulated pulses when the accumulated pulses reach a pre-determined threshold, e.g., pulse count, time etc. Using this method, the frequency of each individual pulse string released or output from the accumulator may vary slightly from the expected frequency of the Doppler echo pulse depending upon the clock frequency, threshold, etc. However, the average of these accumulated pulses will, on a time average basis, be correctly shifted from the original Doppler pulses to provide accurate echo pulses. Such a process is illustrated in and described below with reference to FIG. 9.

Figure 6A:
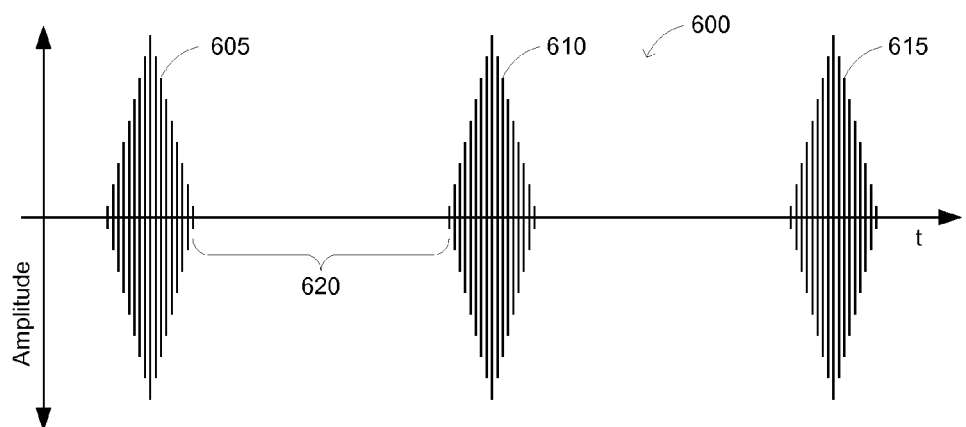
FIGS. 6A-6C illustrate views of a signal from an acoustic system that may be tested using embodiments of the present invention.
Figure 6B:
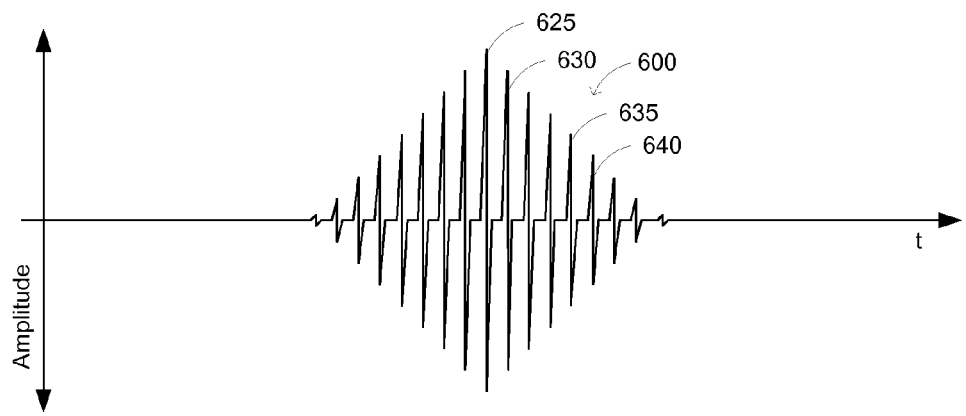
Figure 6C:
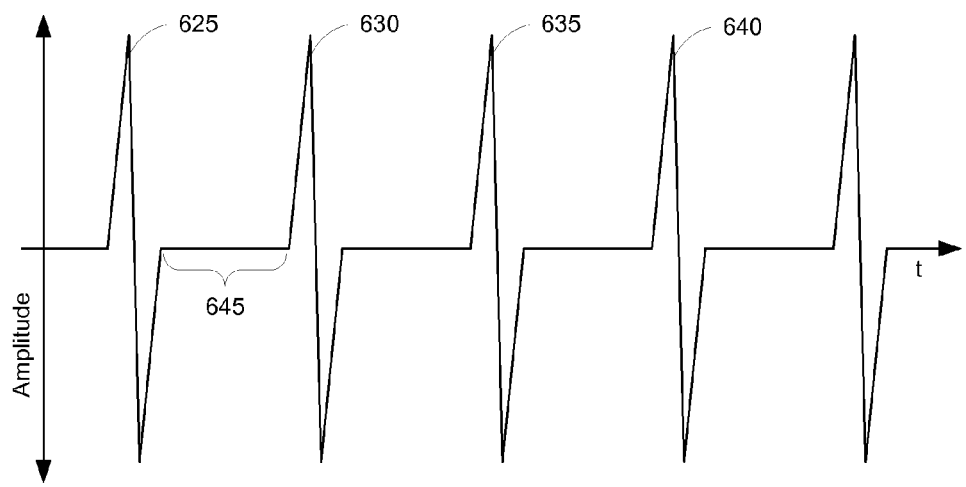

FIGS. 6A-6C illustrate views of a signal from an acoustic system that may be tested using embodiments of the present invention. More specifically, FIG. 6A illustrates a signal 600 comprising a series of bursts 605, 610, and 615. Each of these bursts 605, 610, and 615 can be comprised of a series of pulses. For example, FIG. 6B illustrates a view of an individual burst 605 in which a series of pulses 625, 630, 635, and 640 can be seen. FIG. 6C illustrates yet another view in which a series of pulses 625, 630, 635, and 640 can be seen.

As described below, a pattern matching process can be implemented which distinguishes between two or more different types of pulses. For example, a distinction can be made between the bursts 605, 610, and 615 illustrated in FIG. 6A and the individual pulses 625, 630, 635, and 640 illustrated in FIG. 6C. This distinction can be made based on a difference in a time between bursts, e.g., the time 620 between burst 605 and burst 610, and the time between individual pulses, e.g., a time 645 between individual pulse 625 and individual pulse 630. Thus, based on the time between pulses, pattern matching can be performed in which a distinction can be made between a first type of pulse (referred to in the following example as pulse type B), e.g., a beginning of a burst, and a second type of pulse (referred to in the following example as pulse type A), e.g., a pulse occurring within a burst.

Figure 7:
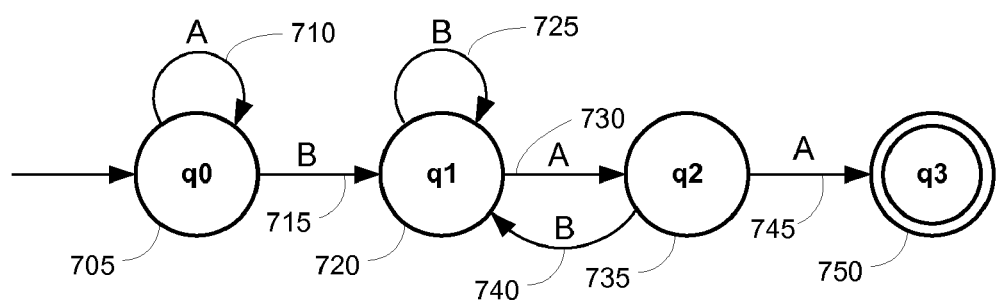
FIG. 7 a diagram illustrating a state machine for implementing a pattern matching process according to one embodiment of the present invention.

FIG. 7 a diagram illustrating a state machine for implementing a pattern matching process according to one embodiment of the present invention. In this example, state q0 705 loops 710 until a first pulse type (type B) is detected 715, e.g., based on the time delay before that pulse and since a previous one. In other words, state q0 705 finds the beginning of a burst. At state q1 720, if another pulse of type B is detected, state q1 720 loops 725 until a second pulse type (type A) is detected. In other words, state q1 710 finds a pulse within the burst. When state q1 720 detects 730 the a type A pulse, state q2 735 confirms the pulse type. If state q2 735 detects a pulse type B, the process returns 740 to state q1 720. However, if state q2 735 confirms 745 a pulse type A, state q3 750 can capture the detected pulse. According to one embodiment, capturing the pulse can further include determining if the pulse is the largest of that pulse type encountered. That is, pulses of the second type (type A) can be discarded or not saved other than the highest amplitude pulse of that type, typically occurring in or near the middle of a burst such that the state machine can determine or identify the highest amplitude pulse for a particular acoustic system configuration under test.

While this process can be implemented by a state machine such as a Deterministic Finite Automaton (DFA), it should be understood that other implementations are possible. That is, while the process above is described with reference to various states of a state machine, such an implementation is provided for illustrative purposes only and is not intended to limit the scope of the present invention. Thus, various other implementations of such a process are contemplated and considered to be within the scope of the present invention. Furthermore, while only one state machine is described here for the sake of clarity and brevity, it should be understood that multiple state machines may be implemented by a given testing device depending upon the implementation. For example, the state machines may be general, to be used in many configurations of the acoustic system under test, or they may be specific, used for a particular system or configuration. According to one embodiment, the state machines for the system and/or configuration under test can be determined a priori using various techniques and obtained by the host computer over the Internet from a database and provided from the host computer to the testing device.

Figure 8:
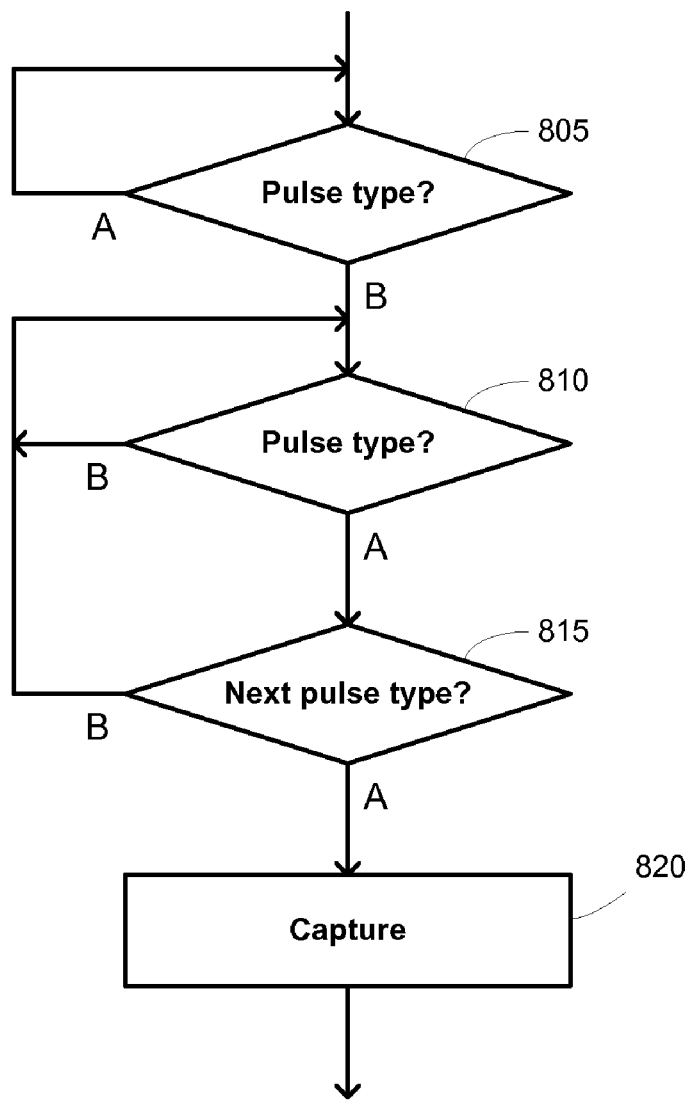
FIG. 8 is a flowchart illustrating another view of a process for performing pattern matching according to one embodiment of the present invention.

FIG. 8 is a flowchart illustrating another view of a process for performing pattern matching according to one embodiment of the present invention. In this example, matching the pattern of pulses to an expected pulse pattern for the acoustic system can begin with determining 805 whether the pulse pattern includes a first pulse type (e.g., pulse type B). If 805 the pulse pattern does not include the first pulse type, processing can loop or continue checking the pulse pattern until the first pulse type is found. In response to determining 805 the pulse pattern includes the first pulse type, a determination 810 can be made as to whether the pulse pattern further includes a second pulse type (e.g., pulse type A). If 810 the pulse pattern does not include the second pulse type, processing can loop or continue checking the pulse pattern until the second pulse type is found. In response to determining 810 the pulse pattern further includes the second pulse type a subsequent pulse of the second pulse type can be identified 815 and captured 820. If the subsequent pulse of the second type cannot be identified 815 or another pulse type is encountered, processing can return to determining 810 whether the pulse pattern further includes the second pulse type.

Figure 9:
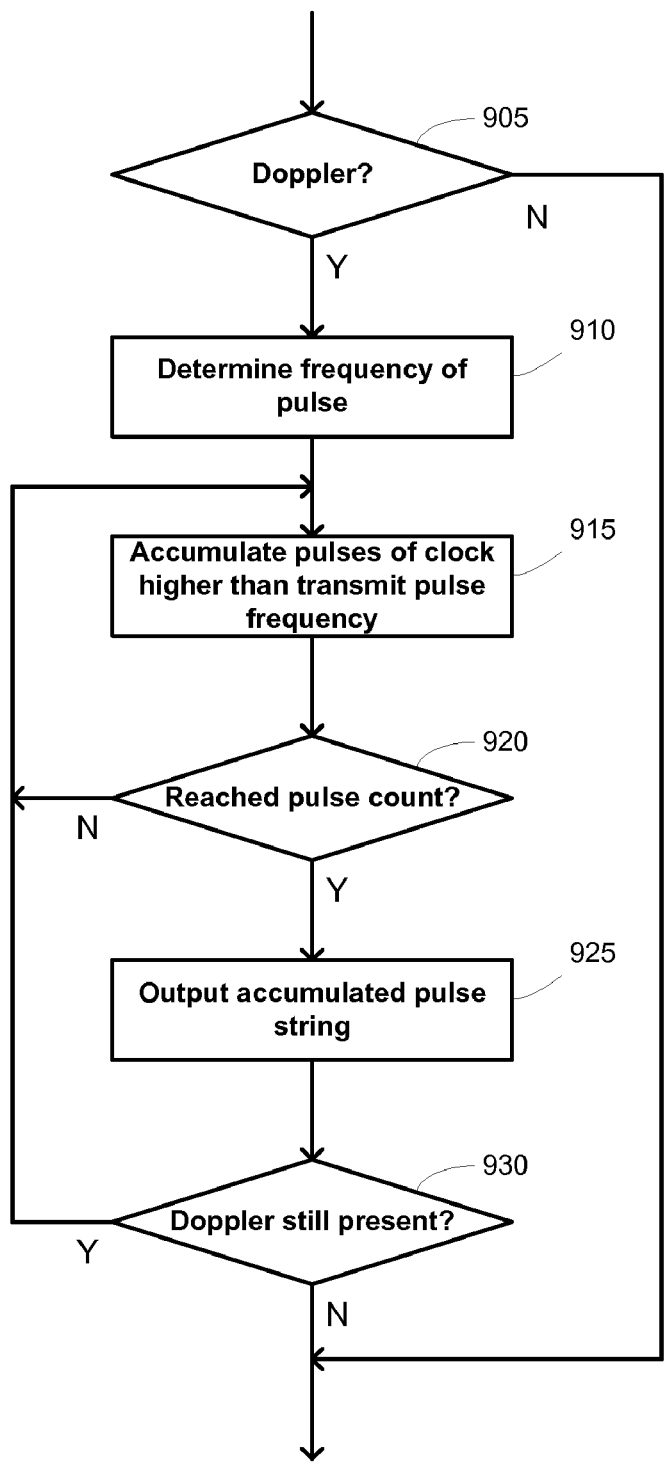
FIG. 9 is a flowchart illustrating a process for responding to a Doppler transmit pulse of an acoustic system according to one embodiment of the present invention.

FIG. 9 is a flowchart illustrating a process for responding to a Doppler transmit pulse of an acoustic system according to one embodiment of the present invention. In this example, generating the echo pulse can comprise determining 905 whether the signal includes Doppler pulses. If 905 Doppler pulses are present, a frequency of the Doppler pulses can be determined 910. Determining 910 the frequency of the Doppler pulses can be based on a value determined a priori, e.g., from the acoustic system specifications stored in a database accessible by the host computer and provided to the testing device from the host computer. According to an alternative implementation, the frequency can be obtained from the acoustic system using a calibration routine involving user feedback to back out the frequency. According to yet another alternative implementation, the frequency can be determined by measuring the frequency of the received pulses at the testing device, i.e., as part of capturing and analyzing pulses from the acoustic system.

Regardless of exactly how the frequency is determined, pulses of a clock having a frequency higher than the frequency of the Doppler pulses can be accumulated 915. A determination 920 can be made as to whether the accumulated pulses have reached a pre-determined threshold, e.g., pulse count, time etc. If 920 the accumulated pulses have reached the pre-determined threshold, the accumulated pulses can be output 925. Accumulating pulses 915 of the clock and outputting 925 the accumulated pulses can be repeated while 930 the Doppler pulses are present in the signal. As noted above, while the frequency of each individual pulse string released or output from the accumulator may vary slightly from the expected frequency of the Doppler echo pulse depending upon the clock frequency, threshold, etc., the average of these accumulated pulses will, on a time average basis, be correctly shifted from the original Doppler pulses to provide accurate echo pulses.

In the foregoing description, for the purposes of illustration, methods were described in a particular order. It should be appreciated that in alternate embodiments, the methods may be performed in a different order than that described. It should also be appreciated that the methods described above may be performed by hardware components or may be embodied in sequences of machine-executable instructions, which may be used to cause a machine, such as a general-purpose or special-purpose processor or logic circuits programmed with the instructions to perform the methods. These machine-executable instructions may be stored on one or more machine readable mediums, such as CD-ROMs or other type of optical disks, floppy diskettes, ROMs, RAMs, EPROMs, EEPROMs, magnetic or optical cards, flash memory, or other types of machine-readable mediums suitable for storing electronic instructions. Alternatively, the methods may be performed by a combination of hardware and software.

While illustrative and presently preferred embodiments of the invention have been described in detail herein, it is to be understood that the inventive concepts may be otherwise variously embodied and employed, and that the appended claims are intended to be construed to include such variations, except as limited by the prior art.

What is claimed is:

1. A method for testing an acoustic system, the method comprising:
   receiving a signal from the acoustic system at a testing device coupled with the acoustic system via one of a plurality of channels between the acoustic system and the testing device, wherein the signal includes a pattern of pulses;
   detecting at least one pulse from the pattern of pulses of the signal with the testing device, wherein detecting the at least one pulse comprises matching the pattern of pulses to an expected pulse pattern for the acoustic system; and
   responding to the signal from the acoustic system by generating an echo pulse with the testing device based on the detected at least one pulse wherein the echo pulse mimics a response to the detected at least one pulse for a selected acoustic pulse.

2. The method of claim 1, wherein matching the pattern of pulses to an expected pulse pattern for the acoustic system comprises:
   determining whether the pulse pattern includes a first pulse type;
   in response to determining the pulse pattern includes the first pulse type, determining whether the pulse pattern further includes a second pulse type; and
   in response to determining the pulse pattern further includes the second pulse type, detecting a subsequent pulse of the second pulse type.

3. The method of claim 2, wherein matching the pattern of pulses to an expected pulse pattern for a selected acoustic probe is performed by a Deterministic Finite Automaton.

4. The method of claim 2, wherein the first pulse type and the second pulse type are distinguished based on a time between adjacent pulses.

5. The method of claim 4, further comprising prior to receiving the signal from the acoustic system, receiving a selection of the selected acoustic probe at the testing device.

6. The method of claim 5, wherein receiving the selection of the selected acoustic probe comprises receiving probe specific data for the selected acoustic probe and system specific data for the acoustic system.

7. The method of claim 6, wherein the system specific data includes information indicating a time between adjacent pulses for the first pulse type and a time between adjacent pulses for the second pulse type and wherein matching the pattern of pulses to an expected pulse pattern for the acoustic system is based on the system specific data.

8. A system for testing an acoustic system including a testing device, the testing device comprising:
   an interface adapted to communicatively interface with a plurality of channels of the acoustic system;
   a switch matrix communicatively coupled with the interface and adapted to select one of the plurality of channels and receive a signal from the acoustic system via the selected one of a plurality of channels, wherein the signal includes a pattern of pulses;

a pulse detection module communicatively coupled with the switch matrix and adapted to detect at least one pulse from the pattern of pulses of the signal;

an echo pulse synthesizer communicatively coupled with the switch matrix and pulse detection module and adapted to respond to the signal from the acoustic system by generating an echo pulse based on the detected at least one pulse wherein the echo pulse mimics a response to the detected at least one pulse for a selected acoustic probe; and a computational unit communicatively coupled with the interface, switch matrix, pulse detection module, and echo pulse synthesizer, wherein the computational unit is adapted to match the pattern of pulses to an expected pulse pattern for the acoustic system.

9. The system of claim 8, wherein matching the pattern of pulses to an expected pulse pattern for the acoustic system comprises:

determining whether the pulse pattern includes a first pulse type;

in response to determining the pulse pattern includes the first pulse type, determining whether the pulse pattern further includes a second pulse type; and in response to determining the pulse pattern further includes the second pulse type, detecting a subsequent pulse of the second pulse type.

10. The system of claim 9, wherein matching the pattern of pulses to an expected pulse pattern for a selected acoustic probe is performed by a Deterministic Finite Automaton.

11. The system of claim 9, wherein the first pulse type and the second pulse type are distinguished based on a time between adjacent pulses.

12. The system of claim 11, further comprising a host computer communicatively coupled with the computational unit of the testing device wherein, prior to receiving the signal from the acoustic system, the computational unit receives a selection of the selected acoustic probe.

13. The system of claim 12, wherein receiving the selection of the selected acoustic probe comprises receiving probe specific data for the selected acoustic probe and system specific data for the acoustic system.

14. The system of claim 13, wherein the system specific data includes information indicating a time between adjacent pulses for the first pulse type and a time between adjacent pulses for the second pulse type and wherein matching the pattern of pulses to an expected pulse pattern for the acoustic system is based on the system specific data.

15. A nontransitory machine-readable medium having stored thereon a series of instructions which, when executed by a processor, cause the processor to test an acoustic system by:

receiving a signal from the acoustic system at a testing device coupled with the acoustic system via one of a plurality of channels between the acoustic system and the testing device, wherein the signal includes a pattern of pulses;

detecting at least one pulse from the pattern of pulses of the signal with the testing device, wherein detecting the at least one pulse comprises matching the pattern of pulses to an expected pulse pattern for the acoustic system; and responding to the signal from the acoustic system by generating an echo pulse with the testing device based on the detected at least one pulse wherein the echo pulse mimics a response to the detected at least one pulse for a selected acoustic probe.

16. The nontransitory machine-readable medium of claim 15, wherein matching the pattern of pulses to an expected pulse pattern for the acoustic system comprises:

determining whether the pulse pattern includes a first pulse type;

in response to determining the pulse pattern includes the first pulse type, determining whether the pulse pattern further includes a second pulse type; and in response to determining the pulse pattern further includes the second pulse type, detecting a subsequent pulse of the second pulse type.

17. The nontransitory machine-readable medium of claim 16, wherein matching the pattern of pulses to an expected pulse pattern for a selected acoustic probe is performed by a Deterministic Finite Automaton.

18. The nontransitory machine-readable medium of claim 16, wherein the first pulse type and the second pulse type are distinguished based on a time between adjacent pulses.

19. The nontransitory machine-readable medium of claim 18, further comprising prior to receiving the signal from the acoustic system, receiving a selection of the selected acoustic probe at the testing device.

20. The nontransitory machine-readable medium of claim 19, wherein receiving the selection of the selected acoustic probe comprises receiving probe specific data for the selected acoustic probe and system specific data for the acoustic system.

21. The nontransitory machine-readable medium of claim 20, wherein the system specific data includes information indicating a time between adjacent pulses for the first pulse type and a time between adjacent pulses for the second pulse type and wherein matching the pattern of pulses to an expected pulse pattern for the acoustic system is based on the system specific data.

* * * * *